(12) United States Patent
Ronnekleiv et al.

(10) Patent No.: US 7,003,184 B2
(45) Date of Patent: Feb. 21, 2006

(54) FIBER OPTIC PROBES

(75) Inventors: Erlend Ronnekleiv, Trondheim (NO); Arne Berg, Kattem (NO); Jon Thomas Kringlebotn, Trondheim (NO); Reinold Ellingsen, Trondheim (NO); Dag Roar Hjeime, Trondheim (NO)

(73) Assignee: OptoMed. AS, Trondheim (NO)

( * ) Notice: Subject to any disclaimer, the term of this patent is extended or adjusted under 35 U.S.C. 154(b) by 131 days.

(21) Appl. No.: 09/950,252

(22) Filed: Sep. 7, 2001

(65) Prior Publication Data
US 2002/0041724 A1 Apr. 11, 2002

(30) Foreign Application Priority Data
Sep. 7, 2000 (GB) .................................. 0021975

(51) Int. Cl.
*G02B 6/00* (2006.01)
(52) U.S. Cl. .......................................... 385/12; 385/13
(58) Field of Classification Search .................. 385/12, 385/13; 606/12
See application file for complete search history.

(56) References Cited

U.S. PATENT DOCUMENTS

| | | | |
|---|---|---|---|
| 4,842,403 A | 6/1989 | Tarbox et al. | |
| 4,842,783 A * | 6/1989 | Blaylock | 264/1.27 |
| 4,873,989 A | 10/1989 | Einzig | |
| 5,348,019 A | 9/1994 | Sluss, Jr. et al. | |
| 5,452,393 A | 9/1995 | Stowe et al. | |
| 5,564,832 A | 10/1996 | Ball et al. | |
| 5,744,794 A | 4/1998 | Michie et al. | |
| 5,828,059 A | 10/1998 | Udd | |
| 5,844,927 A | 12/1998 | Kringlebotn | |
| 6,097,487 A | 8/2000 | Kringlebotn et al. | |
| 6,492,636 B1 * | 12/2002 | Chen et al. | 250/227.14 |

FOREIGN PATENT DOCUMENTS

| | | |
|---|---|---|
| EP | 0 392 897 | 10/1990 |
| GB | 2 196 424 A | 4/1988 |
| GB | 2 308 888 A | 7/1997 |
| GB | 2 326 471 A | 12/1998 |
| WO | WO 88/00023 | 1/1988 |
| WO | WO 94/17366 | 8/1994 |
| WO | WO 94/20013 | 9/1994 |
| WO | WO 98/36252 | 8/1998 |

OTHER PUBLICATIONS

Rao et al, "In-Fiber Bragg-Grating Temperature Sensor System for Medical Applications", May 1997, IEEE, Journal of Lightwave Technology, vol. 15, No. 5, pp. 779-785.*

(Continued)

*Primary Examiner*—Drew A. Dunn
*Assistant Examiner*—Joshua L. Pritchett
(74) *Attorney, Agent, or Firm*—McCormick, Paulding & Huber LLP

(57) ABSTRACT

A body compatible fiber optic sensor probe for invasive medical use is provided. The probe includes at least one sensing location at which the fiber is configured to provide at least one detectable changeable optical property responsive to strain within the fiber, and at least one sensing element which undergoes a volumetric change in response to an in body parameter to be sensed. The sensing element is coupled to the fiber in such a way that the volumetric change induces strain within the fiber so as to vary the detectable optical property or properties.

144 Claims, 7 Drawing Sheets

OTHER PUBLICATIONS

Othonos et al, Fiber Bragg Gratings, 1999, Artech House, Inc., pp. 114-115 & 366.*

U.S. Appl. No. 09/948,427, filed Sep. 7, 2001 entitled "Multi-Parameter Fiber Optic Probes".

M. Shibayama and T. Tanaka, "Volume Phase Transition and Related Phenomena of Polymer Gels", in Advances in Polymer Science, vol. 109, Springer Verlag 1993.

T. Miyata et al., "A Reversibly Antigen-Responsive Hydrogel", Nature, vol. 399, pp. 766-769, Jun. 24, 1999.

* cited by examiner

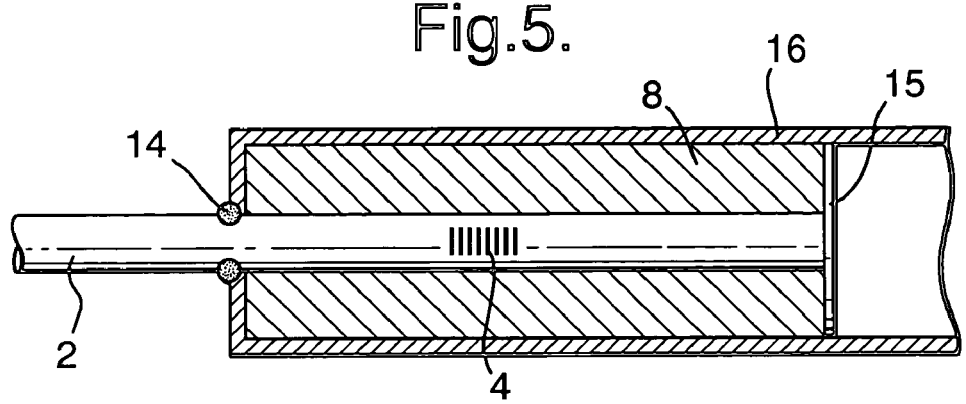
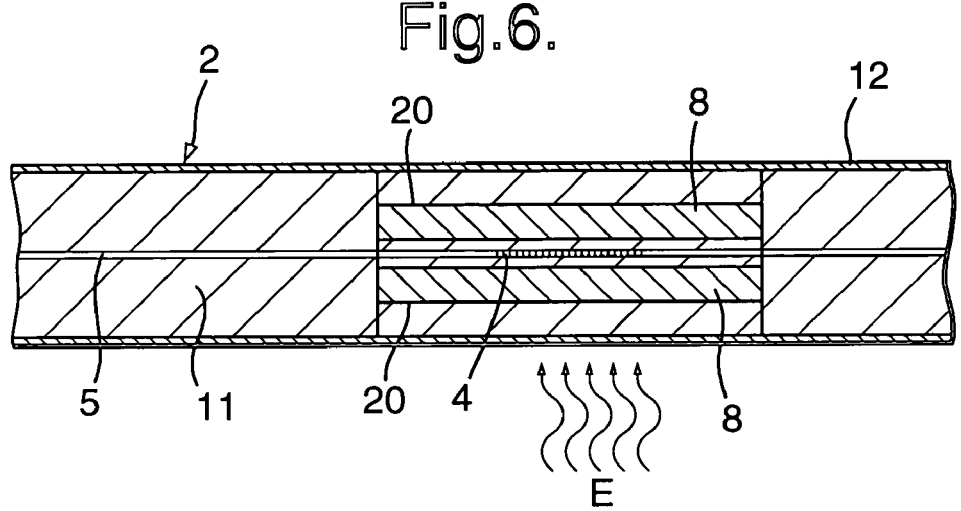
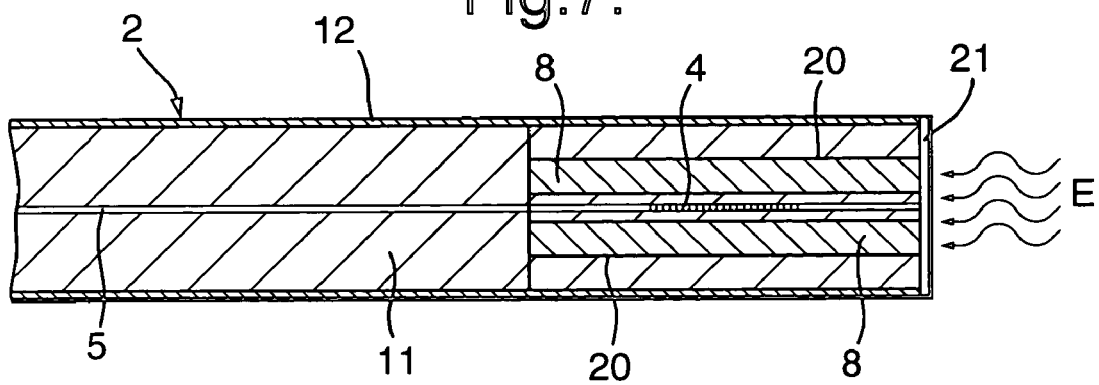

FIBER OPTIC PROBES

This application is entitled to the benefit of, claims priority from, and incorporates by reference subject matter disclosed in UK Patent Application No. 0021975.8, filed Sep. 7, 2000.

This invention relates to fiber optic probes and sensors, particularly but not exclusively, for invasive medical applications used in the measurement of at least one parameter within the body. These parameters (measurands) include pressure, differential pressure, radiation, fluid flow, temperature, and biological parameters such as concentration of particular chemical and biological substances at one or a number of measuring locations within the body. The invention also extends to methods of medical treatment and diagnosis which employ the fiber optic probes of the invention. Whilst some aspects of the invention relate to in vivo medical applications, features and aspects of the probes may also find application in other measuring context, such as ex-vivo or in vitro medical uses.

With the advance of technology relating to medical diagnosis and therapy there is an on-going need to improve methods and systems for sensing various physical, chemical and biological parameters within the body. Such sensing is needed both during diagnosis and during treatment. Further, there is increasing emphasis on the use of minimally invasive medical techniques, intended to reduce the trauma to the patient during and following medical procedures. In this respect, given their small dimensions, fiber optic devices are commonly used in various aspects of medicine, for example for viewing a treatment site via an endoscope, for delivery of laser therapy within the body, and in the context of optical biochemical sensors for monitoring and measuring various parameters.

Prior art biochemical sensors for medical use have generally included a coating or reagent provided on the end face of a waveguide provided at or defined by the distal end of the optical fiber, or at the core-cladding interface of such a fiber. Such a coating or reagent is intended to react with a target substance, in such a way as to directly change the optical response of the sensor. The sensing mechanisms may be chemical systems whose spectra change under the effect of certain reactions, or dielectrics which change refractive index through induced swelling or another mechanism.

Changes in this reactive coating can be observed through known spectroscopy techniques, fluorescence techniques, or interferometric techniques.

There remains, however, a need for improved body implantable, fiber optic sensor probes. In particular, the known optical biochemical sensors all operate through direct interaction between the reactant coating and the light which is passed down the fiber optic cable to detect the change in optical response. This places restrictions on the kind of coatings/reagents which can be used, since they must have the dual purpose of responding to a particular measurand, and interacting with the light to provide the required response. For example, the coating must be optically transparent, resistant to photo bleaching of the reagent, and resistant against any photo degradation due to the applied light. Because of these difficulties there is a tendency to use low light levels, which can impact unfavourably on the dynamic range and sensitivity of such sensors. Further, fluorescence in some coatings can impair performance.

A first aspect of the invention provides a body compatible fiber optic sensor probe for invasive medical use, such a probe including at least one sensing location at which the fiber is configured to provide at least one detectable changeable optical property responsive to strain within the fiber, and at least one sensing element which undergoes a volumetric change in response to an in body parameter to be sensed, the sensing element being coupled to the fiber in such a way that the volumetric change induces strain within the fiber so as to vary its detectable optical property or properties.

The invention extends to sterile medical probes as described above and below, and to sterile packs including such probes.

A further aspect of the invention provides methods of treatment or diagnosis of the human or animal body which use any of the probes described herein.

The above aspect of the invention represents a new departure in the context of medical fiber optic probes in that the probe may be configured to operate without interaction between the light used to detect the change in the fiber's optical properties and the sensing element. This means that the difficulties associated with the prior art, such as photo degradation and photo bleaching of the sensing element, self-absorption by the element, and the need to use a transparent element with relatively low intensities, can be avoided.

This is because, according to the invention, the sensing element operates by providing a physical strain i.e. mechanical distortion within the optical fiber in order to obtain the change in optical response of the probe. As discussed below, this strain may be generally longitudinally, transversely and/or generally radially directed.

Preferably the sensing element comprises a mass of reactive material.

The varying optical property or properties of the fiber at the sensing location can be provided by a variety of known methods. For example, the fiber may be configured by known means to provide a form of "Fabry-Perot" interferometer, in which there are, in effect, spaced "mirrors" within the fiber whose spacing will determine the wavelength of transmitted and reflected light by the interferometer. In such an arrangement, the sensing element of the invention is configured to provide compressive or extensive longitudinal strain within the fiber, such that the mirror spacing changes and that there is a detectable change in the interference pattern established by the reflected light. Other such interferometric techniques are known. Through the use of appropriate interrogating means and light sources, high resolution strain measurements, and hence measurement of a particular parameter, can be obtained.

An alternative and preferred optical sensing mechanism for a probe according to the invention involves one or more fiber Bragg gratings (FBG's) written into the optical fiber core. Passive and active FBG's are known in optical fiber sensors used in other contexts, such as strain measurement in civil engineering structures and downhole temperature and pressure measurement in gas and oil exploration.

Optical fiber Bragg gratings are made by producing periodic variations in the refraction index along a short section in the core of an optical fiber. There are a number of known fabrication techniques in this respect.

Passive FBG sensors are known in which the gratings couple fiber modes into their reverse propagating mode at a wavelength in the core that is twice the spacing of the Bragg grating. A change in longitudinal strain on the fiber changes the spacing and hence the Bragg wavelength of the reflected light. An example of such a system is described in U.S. Pat. No. 6,097,487.

It is also known in such FBG devices to provide fiber Bragg gratings in a birefringent optical fiber, such as a fiber provided with side air holes either side of the core or a bow-tie or Panda fiber. In such an arrangement, the spectral peaks or notches of the reflected light are spaced in the different polarization planes, and the detectable distance between the peaks or notches depends on the radial stress applied to the fiber in the region of the side-holes and the fiber Bragg grating. Such a system is described, for example, in U.S. Pat. No. 5,828,059. In this way, the fiber can be used to sense both radial pressure and longitudinal strain, in that the spectral peak or notch spacing, as discussed, is pressure dependent, whereas the absolute wavelengths of components of the spectrum are longitudinal strain dependent. As discussed below, this means that a medical fiber optic probe according to the invention can be configured to detect, simultaneously, different measurands. This is particularly the subject of our co-pending application entitled "Multi-Parameter Fiber Optic Probes" lodged simultaneously herewith.

A further preferred sensing method suitable for the probes of the present invention involves the use of active fiber lasers, particularly active FBG lasers. Such devices for use in fiber optic sensors are described, for example, in U.S. Pat. No. 5,844,927 and U.S. Pat. No. 5,564,832. In such systems, an end-pumped fiber laser with distributed feedback (DFB) oscillates on two orthogonally polarised wavelengths. Again, the distance between these wavelengths may be tuned by changing the birefringence of the fiber. The absolute wavelength depends on the grating spacing, so that such an active device can be responsive both to radial and longitudinal strain within the fiber. U.S. Pat. Nos. 5,844,927 and 5,564,832 describe optical light sources, and detectors and signal processing equipment which can be used to detect the Bragg wavelength, together with the wavelength difference in the polarization axes, and these and other known interrogating systems are suitable for use in the present invention.

Viewed from a further aspect the invention provides a body compatible fiber optic probe for invasive medical use which is configured to provide in at least one sensing location an active fiber laser providing a varying optical output in use dependent upon at least one parameter to be measured within a human or animal body.

A still further aspect of the invention provides a body compatible fiber optic probe for invasive medical use which comprises at least one sensing location including an active FBG laser or a passive FBG device providing a birefringent optical output or response dependent upon at least one parameter to be measured within a human or animal body.

Such a system represents a new departure in itself in the context of medical probes.

Both active DFB FBG lasers, and passive DFB FBG devices, represent attractive techniques for high resolution strain measurements in relation to an optical fiber, though, generally, it will be understood that other known detection techniques can be used in probes of the present invention, and each will have different dynamic ranges, sensitivity, and suitability depending on the parameter or parameters to be detected within the body, and on the particular body measurand sensing element which is used in the probe.

The arrangement of the sensing element used in a medical probe according to the invention will vary, depending, for example, on the optical sensing mechanism of the fiber, on the nature of the reactive material which is used for the sensing element, and on the particular parameter or parameters to be measured within the body.

In one set of embodiments the sensing element is in the form of a reactive coating which is disposed directly or indirectly on the fiber cladding. Such a reactive coating may be configured to create radial and/or longitudinal strain within the fiber in such a way as to change its optical response. As discussed below, the coating may be formed of a number of different materials responsive to a selected physical or chemical parameter within the body, such as temperature, pressure, radiation, or particular chemical and biological substances.

A fiber according to this aspect of the invention can include a number of different coated regions spaced along the fiber axis, such that different axial locations along the fiber may be used to sense either the same parameter, or different parameters through the use of different coating materials.

The reactive coating may be formed of a body compatible material such that the coating directly contacts biological material within the body. In a preferred embodiment, however, the coating is provided with an overlying protective membrane, which allows measurement of the particular parameter, but provides a barrier between the coating and the body material. Where such a sensor is a biological or chemical sensor the membrane may allow selected target molecules to diffuse from the body side through to the coating material forming the sensing element.

A further aspect of the invention provides a body compatible fiber optic probe for invasive medical use, wherein at least one sensing location of the fiber is provided with a reactive coating configured to create strain within the fiber responsive to at least one body parameter to be measured, such strain providing a change in at least one detectable optical property of the fiber.

In a particularly preferred embodiment of this aspect of the invention the fiber is configured to change its birefringence in response to swelling or contracting of the coating, such as by means of a fiber provided with one or more side-holes at the sensing location. As described above, radial strain i.e. mechanical distortion within such a fiber will result in a change in birefringence, that is a detectable change in the difference between the wavelength of the optical response of the fiber in its different polarization planes. This system, combined with a reactive coating, provides a particularly accurate fiber optic sensor probe.

In a further set of embodiments of the invention, the sensing element is not coated on the optical fiber, but rather is coupled to the fiber at two or more axially spaced locations, the sensing element expanding or contracting in response to a particular target measurand in order to provide longitudinally directed i.e. axial strain between these locations.

In one such embodiment, the sensing element comprises a cylinder which is fitted over the optical fiber and which is secured thereto at axially spaced locations. In response to a particular measurand the cylinder expands or contracts longitudinally, and therefore creates longitudinal strain within the fiber to cause a changing optical response of the fiber. In an example of such an arrangement, the cylinder may engage a flange extending outwardly from the fiber, the other end of the cylinder being suitably bonded to the fiber, for example through an adhesive.

In a further such embodiment the sensing element may be contained within a cylinder, and arranged to engage a piston carried by or coupled to the fiber. In this way, expansion or contraction of the sensing element within the cylinder again causes the fiber to be longitudinally stretched or compressed, in order to cause the change in optical properties which are detected by the sensing mechanism.

In one such embodiment the sensing element is a solid or semi-solid material located within the cylinder. In another such embodiment the sensing element is flowable liquid or gel which expands within the cylinder in order to apply a longitudinal force on the fiber via the piston.

In embodiments including a piston and cylinder, the cylinder must be formed of a material whereby the measurand to be sensed can cause the volumetric change in the sensing element. Where, for example, the measurand is temperature, then the cylinder should be formed of a material of good thermal conductivity. If the probe is a sensor for chemical or biological material, then the cylinder should be formed of a material which enables the molecules to be sensed to permeate through the cylinder walls so they can contact the sensing element.

Probes of this general design represent a new departure, and may have applications in other fields, such as ex-vivo or in vitro medical uses.

According to a further aspect of the invention there is provided a fiber optic sensor which comprises a sensing element coupled to the fiber at two or more axially spaced locations thereon, and configured to provide a generally axially directed compressive or extensive force on the fiber between such locations in response to a particular parameter to be measured, such a force providing a changing optical response of the fiber.

A still further aspect of the invention provides a fiber optic sensor in which at least one region of the optical fiber provides a varying optical response depending on axial compressive or extensive strain within the fiber, there being a piston and/or cylinder arrangement including a sensing element coupled to said region of the fiber and arranged to provide such strain in response to a parameter to be measured.

In one form of this aspect of the invention, the piston/cylinder arrangement is acted on by two sensing elements arranged to apply force to the fiber in opposite directions. The sensing elements provide a similar response in relation to a first set of parameters, such as temperature and pH value, but a different response in relation to a selected measurand, such as a particular chemical or biochemical substance. In this way measurements of the selected measurand may be compensated for variations in the first set of parameters.

A further set of embodiments of the present invention relate particularly to a fiber optic sensor probe including a fiber such as a fiber provided with one or more side-holes, which provides changing birefringence depending on sideways or radial stress applied to the fiber. As discussed above, such fibers provide a particularly accurate means for detecting stress, particularly when combined with an active fiber laser whose output changes in its different polarisation planes depending on radial distortion of the fiber.

A preferred such embodiment of the invention includes a rigid or semi-rigid housing or sleeve provided around the optical fiber at the sensing location or locations thereof, the sensing element being provided in an annular cavity defined between the housing or sleeve and the fiber such that a radial stress is applied to the fiber in response to a particular parameter which causes expansion or contraction of the sensing element.

This, again, represents a new departure from prior art probes, and may have applications in other fields.

According to a still further aspect of the invention, therefore, there is provided a fiber optic sensor whose optical response changes at one or more measuring locations in response to generally radially applied stress, the fiber being surrounded at such location or locations by a rigid or semi-rigid housing or sleeve, a reactive sensing element being provided between the sleeve and the fiber, the element being arranged to swell in response to a measurand in order to provide strain within the fiber and to change its optical response.

In this aspect, the fiber may advantageously be a side-hole fiber.

As with the other embodiments of the invention, the arrangement should be that the sensing element is sufficiently exposed to the target measurand. In the case of a temperature sensor, the sleeve or housing which surrounds the sensing element is formed of a material with good thermal conductivity such that the sensing element is exposed to changes in temperature and can swell or contract accordingly.

In the case of a chemical or biochemical sensor, the sleeve or housing may be configured to allow the ingress of the target measurand, for example by being a perforate housing or by allowing diffusion of the molecules to be detected through the housing or sleeve wall.

In an alternative embodiment, a sensing element may be provided in one or more side-holes provided in an optical fiber, such that upon exposure to a particular measurand, the element expands to provide sideways strain within the optical fiber. Again, this causes a change in the detectable birefringence of the fiber.

Viewed from a still further aspect, the invention provides an optical fiber sensor in which the optical fiber is provided with one or more side-holes adjacent at least one sensing region of the fiber, a reactive sensing element being provided in one or more side-holes so that the element changes volume to create strain in the fiber in response to one or more measurands to be detected, such strain changing at least one detectable optical property of the fiber.

It will be appreciated that the sensing arrangements of the above embodiments could be combined into a single probe to provide multi-parameter sensing, or to provide compensation in relation to a first parameter for the accurate measurement of a second parameter independently of the first. Various arrangements of this type are described in our aforesaid patent application entitled "Multi-Parameter Fiber Optic Probes" lodged simultaneously herewith.

In further aspects of the invention, the sensing element applies a sideways force on a sensing region of the fiber to establish a bending strain therein, and this causes a change in a detectable optical property or properties of the fiber, for example its birefringence. In a preferred such embodiment, two sensing elements mounted within a housing are arranged to urge a free end of the fiber in opposite directions.

A first sensing element is reactive to a particular chemical or biological substance, and the second sensing element is less sensitive to such substance but is otherwise of similar construction to the first. Hence the effects of other parameters, such as temperature, causing swelling of the sensing elements are cancelled out leaving the sensor responsive only to the particular substance to be measured.

In the embodiments discussed above having the reactive sensing element provided within one or more side-holes of the fiber, it is possible that the fiber be provided with a membrane at a free end thereof which enables a chemical or biological substance to diffuse through the membrane so as to contact the sensing element material within the side-holes. Alternatively, such an embodiment is suitable for use where the target measurand is a form of electromagnetic radiation. In this case, the radiation may pass through the fiber cladding so as to impinge on the sensing material within the side-holes so as to cause a volume change of the material and create strain within the fiber.

The reactive material of which the sensing element used in a probe according to the invention is made will depend on the probe design, and on the parameter to be measured. The reactive material reacts to the presence of the measurand depending on its concentration (in the case of a chemical/biological sensor) or magnitude (in the case of a pressure, radiation or temperature sensor). The material should be highly sensitive in that it should undergo a large volume change for relatively low concentrations or magnitudes of the measurand. As described above, the measurand can react directly with the reactive material, or via an intermediate membrane or layer.

Preferred reactive materials are reactive to non-ionizing radiation, ionizing radiation and chemical or biological, including immunological, interactions.

In certain embodiments of the invention, the reactive material of the sensing element is immobilized on a solid support medium, such as a polymer, copolymer, or various glasses. The immobilization method can be mechanical, electrostatic or chemical. The support medium can remain inert to the reaction being analysed, although in some embodiments it is envisaged that the support could also itself act as a selective element, for example through controlled porosity, to enhance the selectivity of the sensor, and to protect the active medium of the sensor element.

In other embodiments of the invention, for example where the sensing element is located in a cylinder, or within the side-holes of a fiber, it is envisaged that the reactive material of the sensing element could be dispersed or immobilized in a fluid or gel, which swells or contracts in response to a target measurand in order to apply the required stress to the fiber.

In all cases, a separate body compatible membrane covering or enclosing the sensor element can be provided to enhance selectivity of the sensor and protect the active part of the sensor. This membrane can provide selectivity based on size selectivity of the measurand species through controlled porosity of the membrane, chemical/biochemical selectivity through chemical reactions, or ionic selectivity through electrostatic interactions.

In the case of the coating embodiments, the coating can conveniently be made from a form of paint or bonding material such as a polymer gel network, or from a porous material, such as a sol-gel glass or ceramics, to make an open matrix configuration. A further example of a suitable material for use as the sensor is micro-spherical balls, with additives to generate chemical selectivity for a selected group of molecules. Such balls can be confined, for example, within a piston and cylinder, or within a membrane.

One preferred sensing element comprises ionic N-Isopropylacrylamide (NIPA) polymer gel copolymerised by sodium acrylate (SA) which is known to exhibit substantial swelling in an ionic solution. This swelling is a result of an increased osmotic pressure within the gel due to mobile counter ions to the bound cations. As described, for example, in U.S. Pat. No. 5,744,794, hydrogel materials can be formulated of numerous other types and consistencies, and can be prepared to respond to different external stimulii. Those skilled in the art will recognise that hydrogel materials can be formulated to respond to a variety of in body parameters and therefore are particularly suited for use in the sensor probes of the present invention.

The swelling behaviour of polymer gel networks is governed not only by the affinity of polymer chains for solvents, as in the NIPA-SA gel example, but also by the cross-linking density, (see for example M. Shibayama and T. Tanaka, "Volume phase transitions and related phenomena of polymer gels," in Advances in Polymer Science, vol. 109, Springer Verlag, 1993). The cross-linking density controls the elastic restoring force . Affecting the elastic restoring force in turn affects the equilibrium swelling volume of the gel network.

Polymer gel networks responsive to specific biochemicals can therefore also be prepared by application of stimuli-sensitive complex formation at cross-linking points in the gel network, e.g. application of antigen-antibody binding at cross-linking points.

One way to synthesize such materials is to use the well-known polyacrylamide gel system (PAAm) and including the functionalized recognition molecule in the cross-link-co-polymerization reaction. An example of this is described by T Miyata et al., "A reversibly antigen-responsive hydrogel," Nature, vol. 399, pp.766–769, 1999, who used the polyacrylamide gel system to conjugate IgG antibody to prepare an antigen-responsive gel. More specifically they used rabbit immunoglobulin G (rabbit IgG) and goat anti-rabbit IgG (GAR IgG) as the antigen and antibody. Competitive binding of the free antigen (analyte) break the antigen-antibody (receptor) cross-link, thereby reducing the cross-linking density and triggering a change in gel volume.

There are numerous other antigen-antibody or other specific biochemical "key-lock" pairs that can be selected for such biochemical sensitive polymer gel networks, e.g. biotin-avidin and various lectin-saccharide pairs. Any of these can be used to provide the sensing elements of the present invention.

Viewed from a further aspect, the invention provides a body compatible fiber optic probe for invasive medical use, such a probe comprising a sensor element formed from a polymer gel material whose volume changes in response to at least one body parameter to be measured, such change in volume creating strain within the fiber to change at least one detectable optical property thereof.

The use of hydrogel materials in an optical fiber probe for medical use represents a new departure from the prior art, and enables the fabrication of medical probes responsive to a variety of different physical, chemical or biochemical measurands within the body. Suitable hydrogels are known, for example, from U.S. Pat. No. 5,744,794, but have not previously been proposed for use in body implantable medical probes.

The mechanical design of the probes according to the present invention may vary. In all cases, the optical fiber must have a body compatible surface, and is preferably provided with a suitable polymer coating along its length. The probes are sterilised prior to use by any known means.

In the sensing location or locations, the fiber may be provided within a rigid or semi-rigid tubular housing, which encloses and protects the sensing element of the probe.

The housing may be perforate, to enable the body fluids to pass into the housing and to impinge directly on the sensing element, or on the surface of the fiber containing the sensing element.

In an alternative embodiment, the sensing location of the fiber is provided with a removable protective housing, which can be retracted when the fiber sensor is in operation.

In such embodiments, it is also preferred that the sensing element is provided with a protective membrane, which may be of the types described above.

Typical dimensions for a minimally invasive optical fiber probe are that the fiber core diameter is between 4 and 15 $\mu$m, preferably 6 to 10 $\mu$m, and most preferably about 8 $\mu$m.

The fiber cladding diameter may be within the range of 80 to 200 μm, preferably 100 to 150 μm, and most preferably about 125 μm.

Where there is a protective sleeve or housing enclosing the sensing region of the probe, this may have a diameter of the order of 0.2 to 2 mm. In those embodiments having a reactive coating forming the sensing element, the thickness of the coating may vary depending on the coating material and the parameter to be sensed, and typical coating thicknesses may be between 10 and 1000 μm.

The typical length of an FBG sensor is between 1 and 70 mm, and where there are a plurality of sensing locations, these may be spaced apart at a distance between 1 and 100 mm.

The overall fiber optic probe length may be between 10 and 150 mm. Typically, where the probe is formed of a single fiber optic element the length may be between 10 and 100 mm, and where the probe is formed of multiple axially connected fiber optic elements, the length may be between 20 and 150 mm.

The invention extends to a method of medical or biological treatment, analysis or diagnosis, involving the use in vivo, ex-vivo or in vitro of an optical fiber sensor, such sensor having at least one sensing location having a sensing element coupled to the fiber, and the method further comprising detecting a changing optical property of the fiber dependent on a parameter which causes a volumetric change in the sensing element, such volumetric change creating strain within the fiber whereby the change in optical response is created.

A further aspect of the invention provides a method of medical or biological treatment, analysis or diagnosis, in which an optical fiber sensor is exposed to biochemical or biological material, such sensor including at least one active fiber laser providing an output which changes depending on at least one parameter to be measured relating to the material.

Certain embodiments of the invention will now be described, by way of example only, with reference to the accompanying drawings, wherein:

FIGS. 3 to 7 are partly schematic cross-sectional views of the end portions of third to seventh embodiments of the invention;

Figure 13A:
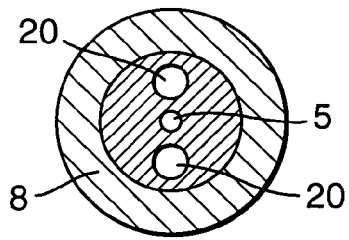
FIGS. 13a and 13b are schematic transverse cross-sectional views showing further embodiments.
Figure 13B:
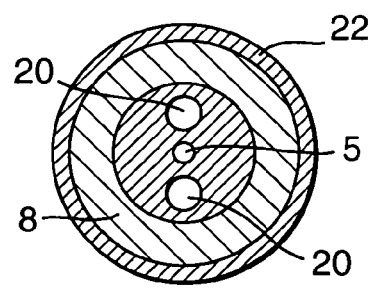
Figure 14A:
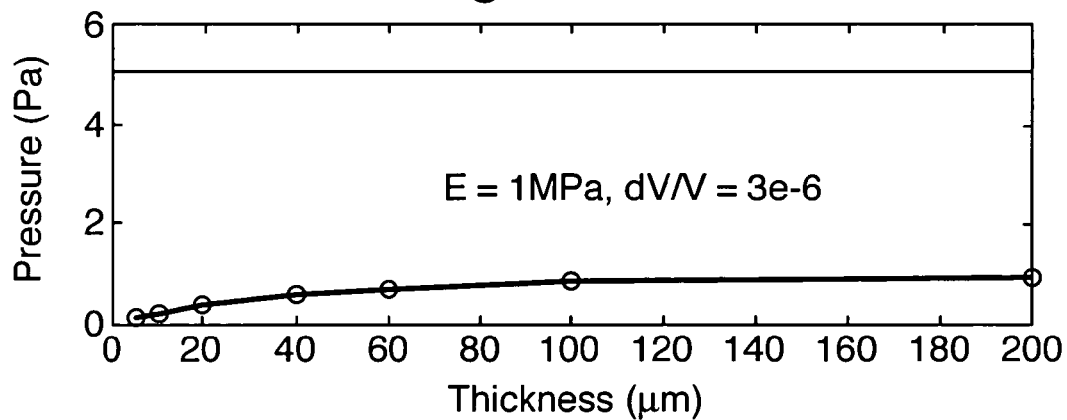
Figure 14B:
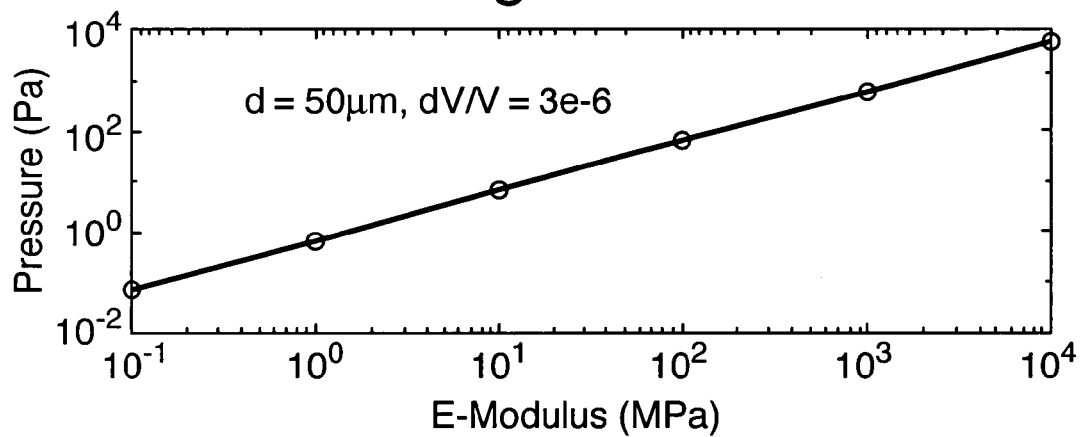
Figure 15:
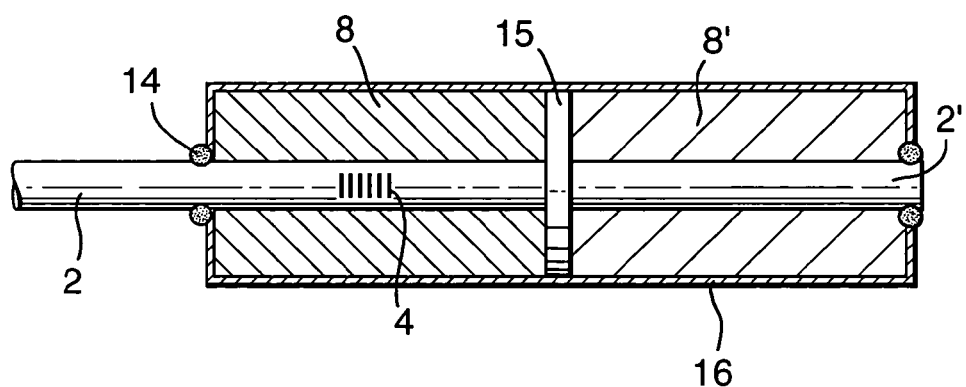
Figure 16A:
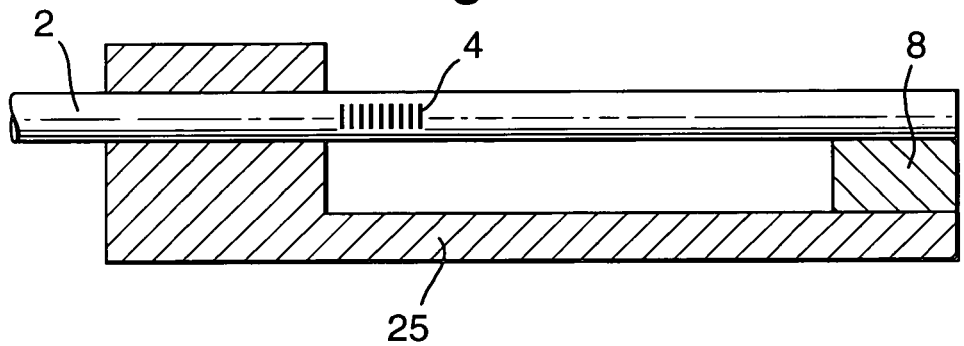
Figure 16B:
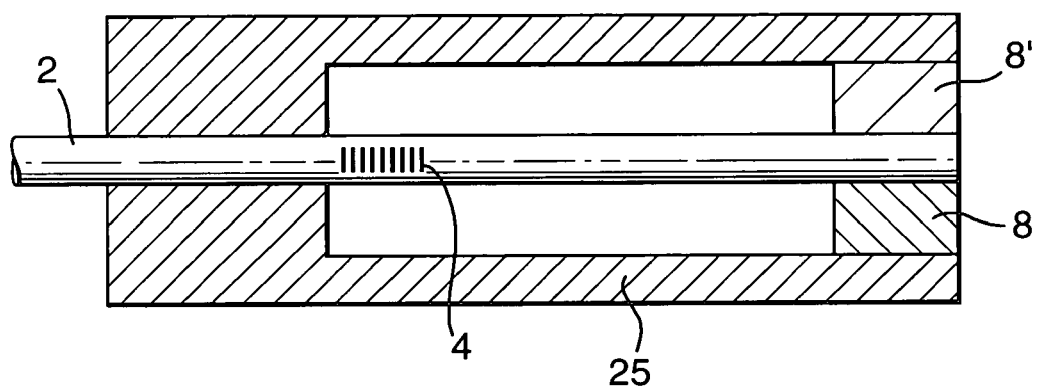
Figure 17:
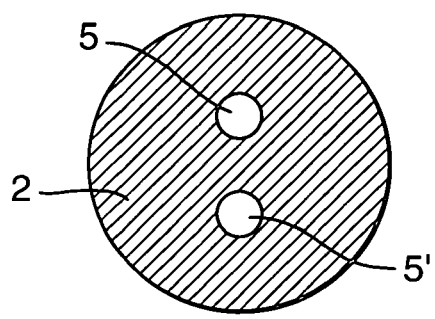

FIGS. 14a and 14b indicate the pressure generated at the fiber cladding upon swelling of the reactive material in the embodiments of FIGS. 13a and 13b;

FIG. 15 is a schematic longitudinal cross-section through a further embodiment;

FIGS. 16a and 16b show alternative embodiments in which a bending strain is established in the fiber; and FIG. 17 is a sideways cross-section through a further embodiment.

Figure 1:
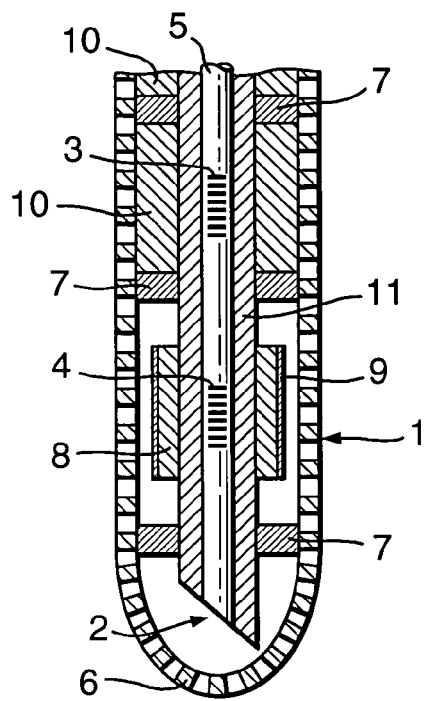
FIG. 1 is a partly schematic cross-sectional view of the distal end portion of a fiber optic sensor probe of a first embodiment of the invention.

Referring to the drawings, in which like reference numerals indicate the same or similar components in the various embodiments, FIG. 1 shows the distal end portion of a first embodiment of optical fiber probe 1 according to a first embodiment of the invention.

The probe consists of an optical fiber 2 provided with optically responsive detectors such as FBG's 3, 4 within the fiber core 5.

The probe includes a body compatible protective tubular housing 6 which encloses and protects the distal end of the fiber 2. The housing 6 is perforated or porous to allow the penetration of body fluids to be measured. The fiber is coupled to the protective housing by a number of annular support members 7 which cooperate between the housing and the fiber 2.

Annular resilient sealing members 10 are provided to prevent the ingress of body fluids beyond the compartment defined by the housing 6 at the distal end of the probe. Provided adjacent a first of the FBG detectors 4 is a sensing element 8 in the form of an annular coating provided directly on the outer surface of the fiber 2. This coating is provided with a protective membrane 9.

As described in detail above, this coating is formed of a suitable material, such as a hydrogel material, which swells in response to a particular parameter, such as temperature, radiation, or a chemical or biological substance, so as to induce a mechanical strain within the fiber in the region of the FBG detector 4. This strain causes mechanical distortion of the fiber and a change in its optical response, which is detected via a suitable known interrogation means (not shown) whereby the target parameter can be measured.

The second FBG detector 3 provides the possibility of temperature compensation, in that it is not coupled to the sensing element 8, and its output can be used together with suitable calibration techniques to avoid the intrinsic thermal expansion/contraction within the fiber interfering with the measurements of the target parameter.

As discussed above, the FBG's may be active or passive detecting devices.

Typical dimensions for the probe shown in FIG. 1 are a fiber core 5 diameter of 8 μm, and a fiber cladding 11 diameter of 125 μm. The thickness of the reactive coating forming the sensor element 8 may vary between 10 and 1000 μm, and the diameter of the outer protective housing 6 may be between 0.2 and 2 mm. The FBG's typically have an individual length of between 1 and 70 mm, and are spaced apart also between 1 and 100 mm. A typical fiber probe length will be between 10 and 100 mm for a single fiber length, and between 20 and 150 mm for a multiple element system.

The fused silica fiber can be protected, e.g. against water, by using a protective coating of a suitable polymer on the fiber cladding 11.

It will be appreciated that, in an alternative embodiment, the outer housing may be omitted, in which case the sensor element coating 8, and the free end of the fiber, can be protected by a suitable body compatible membrane. This membrane, and also the membrane 9 shown in the illustrated embodiment, can be configured to allow the selective ingress of target molecules, in the case of a biological or chemical sensor.

Figure 2:
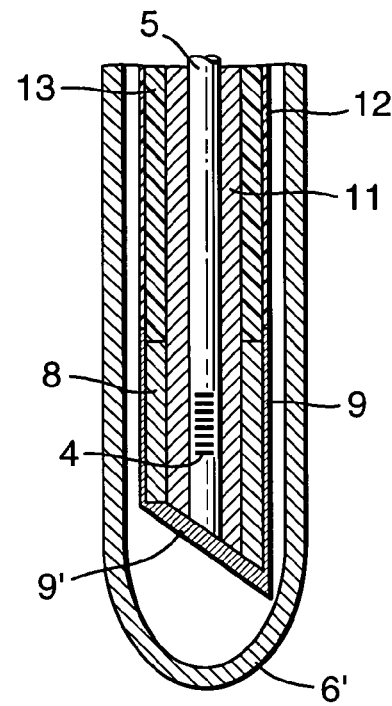
FIG. 2 is a view similar to FIG. 1 of a second embodiment of the invention.

An alternative embodiment is shown in FIG. 2. In this embodiment, the protective housing 6' is sealed, so as to completely protect the sensing element from the outside environment during insertion of the probe into the body. When the probe is in place, the housing and fiber may be moved relative to one another so that the housing is removed from the fiber. In this embodiment the protective membrane 9 includes an additional portion 9' which covers the tip of the fiber, such that the sensing element 8 in the form of a reactive coating is completely covered by a protective membrane. Again, this membrane may allow the selective diffusion of particular molecules through to the reactive coating forming the sensing element 8.

In this embodiment, the length of the fiber is provided with a passive polymer coating 12, and a secondary polymer coating 13 so that the entire length of the fiber is suitably protected.

Figure 3:
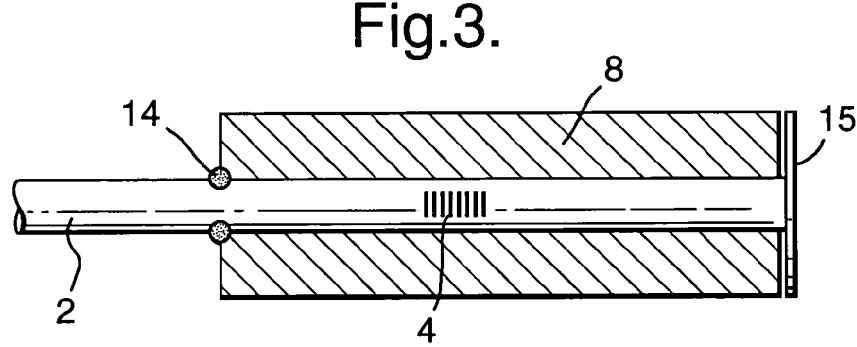

An alternative embodiment is shown in FIG. 3. It should be understood that the embodiments shown in FIG. 3 and the subsequent Figures are illustrated only schematically, and only the principal parts of the sensor are shown. These embodiments could be combined with the housing and more specific features shown in FIGS. 1 and 2.

As illustrated in FIG. 3, the sensing element 8 is in the form of a cylinder of reactive material which expands longitudinally in response to a parameter to be measured, such as temperature, or a chemical or biological parameter.

The cylinder is attached at one end to a first location on the fiber by means of adhesive beads 14.

At its other end it cooperates with the fiber via a flange 15 extending radially outwardly from the distal end of the fiber. At least one active or passive FBG 4 is provided in the fiber core within the sensing element cylinder 8.

The cylinder can be configured when exposed to a measurand to provide strain within the fiber either by longitudinal expansion or contraction. In the latter case, the cylinder needs to be axially fixed to the flange 15. Since the cylinder may also undergo radial contraction or expansion, in those embodiments in which only longitudinal strain is to be detected by the sensor, there can be an axial spacing between the inner wall of the cylinder and the surface of the fiber so that the measurements are unaffected by radial distortion of the fiber.

As in the other embodiments, the cylinder is formed of a suitable material which is responsive to a particular measurand, which can be temperature, pressure, flow, acoustic field, electromagnetic field, ionizing radiation, blood gases, body fluid electrolytes, antibodies and pathogens etc. A preferred material for forming the cylinder can be a relatively solid or semi-solid hydrogel material. Alternatively, the cylinder can be made from a porous sol-gel glass or a ceramic material. Such a material can have the reacting material embedded therein.

Figure 4:
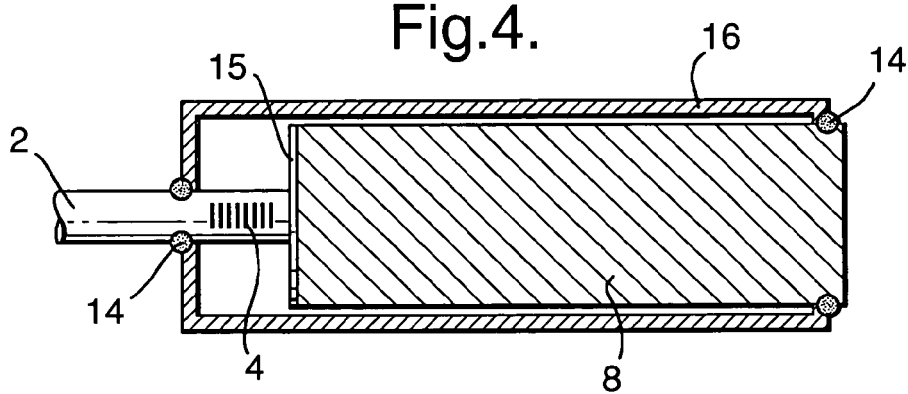

FIG. 4 shows an alternative arrangement in which the sensing element 8 is in the form of a solid piston block of reactive material mounted within a cylindrical housing 16. The optical fiber 2 of the sensor extends through an aperture at one end of the cylinder, and again includes a radially extending flange 15 which is secured to one end of the sensing element 8. The cylinder 16 is adhered to the fiber 2 and to the sensing element 8 by means of suitable beads 14 of adhesive.

When the sensing element 8 is exposed to a measurand, it longitudinally expands or contracts so as to create strain within the fiber 2 in the region of a passive or active FBG detector 4.

The cylinder 16 may be porous, or may be formed of a permeable material, so as to enable analyte fluids, or selected analyte molecules, to pass through the cylinder to the sensing element 8. Alternatively, if the probe is a temperature sensor, then the cylinder 16 is preferably formed of material of good thermal conductivity, and may be filled with a thermally conducting liquid, so as to provide heat transfer to the sensing element.

Again, a temperature compensating FBG can be provided elsewhere along the fiber 2, as in the embodiment shown in FIG. 1.

A still further embodiment is shown in FIG. 5. In this embodiment, the sensor element may be in the form of a fluid or gel confined within the cylinder 16, a flange 15 provided on the end of the fiber constituting a movable piston. When exposed to the parameter to be measured, the gel forming the sensing element 8 expands, whereby the cylinder is urged rightwardly as shown in FIG. 5 to create longitudinal strain within the fiber. This is sensed by means of an active or passive FBG 4. Again, the cylinder 16 can provide permeability for selected analyte molecules. A particularly suitable material for the sensing element 8 in this embodiment is a hydrogel material of the type discussed above, which can be reactive to a variety of different parameters to be measured.

The designs of the probes shown herein allow for multiple cylinders to be provided along the same fiber, making possible a multi-parameter sensor probe by using differently expanding materials, each possessing specific parameter sensitivity. Alternatively, the same parameter can be sensed at different locations using the same reactive material for the sensing element 8. Well-known fiber optic multiplexing techniques, such as Wavelength Division Multiplexing (WDM) and Time Division Multiplexing (TDM) facilitate individual sensing element read-out.

Desirably, the reactive piston or cylinder materials provide diffusivity, repeatability of measurements, and selectivity. The probes shown in FIGS. 3 to 5 can be calibrated using known techniques. A further example of a suitable reactive material, particularly suitable for the FIG. 5 embodiment, comprises micro-spherical balls having additives sensitive to a particular parameter. If the material is intended to be radiation sensitive, then the cylinder 16 shown in FIGS. 4 and 5 should be transparent to the radiation concerned.

Alternative embodiments of the invention are shown in FIGS. 6 and 7. In these embodiments, the reactive material forming the sensing elements 8 is located within side-holes 20 formed in the fiber cladding 11 in the region of the or each FBG detector 4 formed in the fiber core 5. The FBG may be an active or passive device, and in either case the birefringence of the optical output changes in response to the sensing elements 8 expanding within the side-holes 20 so as to distort the fiber.

A preferred such embodiment of birefringent fiber has a single mode core with a typical diameter of 4 to 10 $\mu$m, while the total diameter of the fiber can be anything from 40 to 1000 $\mu$m. If combined with an active fiber laser, such as a fiber distributed feedback laser (DFB), this provides a method for high resolution, accurate measurements of small static strains induced by a measurand impinging on the sensor elements 8. In FIG. 6, the probe is responsive to electromagnetic radiation E, and therefore the outer coating 12 of the fiber is preferably transparent to such radiation, or alternatively may be provided with a window to enable the radiation to pass to the sensing elements 8.

In FIG. 7, the side-holes coincide with the distal end of the fiber, and a transparent covering 21 enables detection of radiation E impinging on the axial end surfaces of the sensing elements 8. Alternatively, the coating may allow the ingress of selected molecules in a chemical or biological sensor. Again, the elements 8 can be formed of a hydrogel material.

Figure 8A:
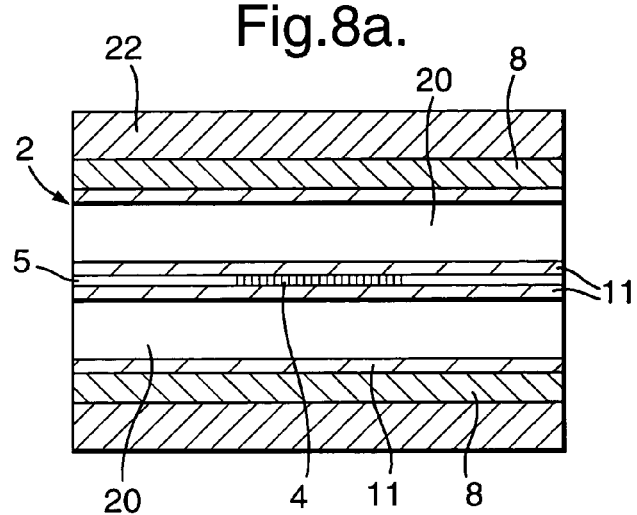
FIGS. 8a and 8b are, respectively, longitudinal and radial cross-sections through an eighth embodiment of a probe according to the invention.
Figure 8B:
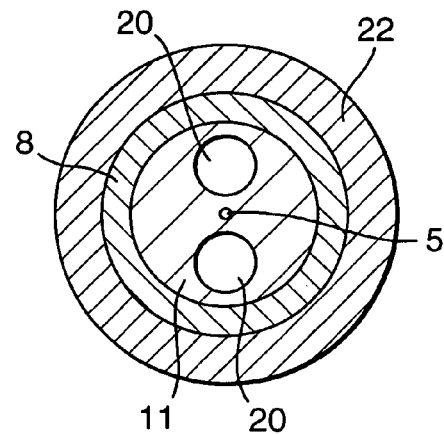

An alternative embodiment involving the use of a side-hole, birefringent fiber is shown in FIGS. 8a and 8b. In this embodiment, a rigid or semi-rigid sleeve 22 surrounds the fiber 2 in the region of the active or passive FBG 4. The material forming the sensing element 8 is located in the annular gap defined between the sleeve 22 and the fiber, such that when the material expands on exposure to a particular measurand, the fiber is radially compressed. Because of the arrangement of the side-holes 20 in the birefringent fiber, such strain is asymmetric, and creates a change in the birefringent response of the fiber, i.e. a change in the detectable wavelength difference between the optical signal in mutually orthogonal polarization planes.

Figure 9A:
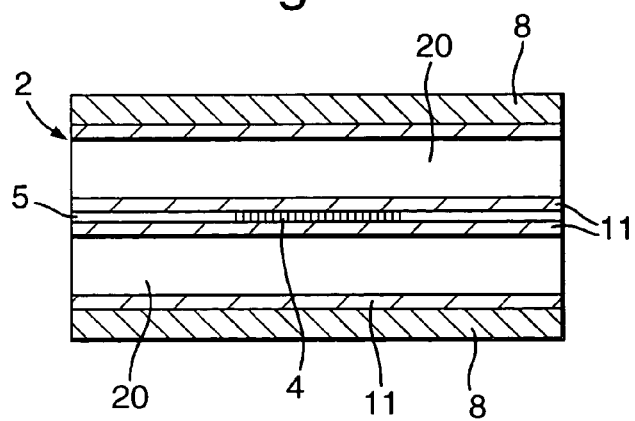
FIGS. 9a and 9b are longitudinal and radial cross-sections through a ninth embodiment.
Figure 9B:
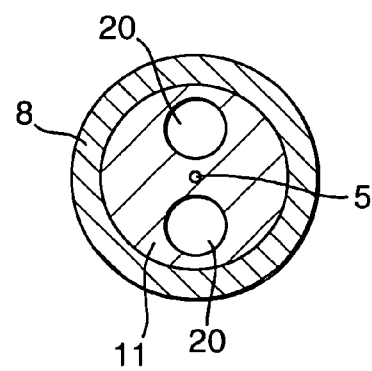

As shown in FIGS. 9a and 9b, a passive FBG or fiber DFB laser forms the detecting means 4 of a probe comprising two side-holes 20 normally filled with air. A sensing element 8 in the form of an expanding hydrogel coating is provided on the outside surface of the fiber, in the region of the or each FBG/DFB device. In this embodiment, the coating responds to a chemical substance diffusing into this layer, which can be directly exposed to body fluids.

The expanding/contracting layer of the sensing element 8 causes longitudinal strain within the fiber which, as discussed above, results in a shift in the Bragg wavelength of the sensor. The expanding and contracting layer also results in a radial negative or positive pressure on the fiber, which due to the side-hole structure of the fiber causes a birefringence, and a change in wavelength splitting of the two orthogonally polarized reflection peaks of a passive device, or a change in the splitting between the two orthogonally polarized frequencies of a fiber laser. Through suitable calibration of these characteristics, an accurate sensor for measuring swelling caused by the indiffusion of chemical or biological substances can be provided. FIGS. 10a to 10d illustrate some theoretical characteristics of the sensor shown in FIGS. 9a and 9b, which are based on the Flory-Rehner theory and on the classic theory of elasticity. Through these theories, it is possible to quantify the radial pressure and longitudinal strain caused by the swelling/contracting layer.

Figure 10A:
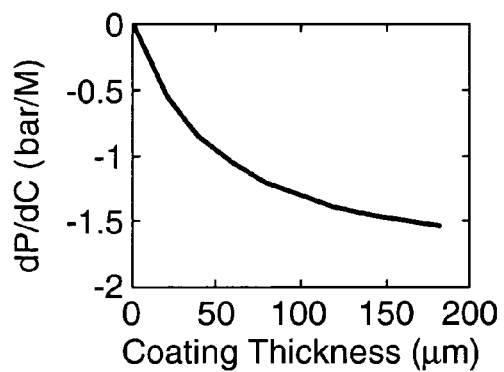
FIGS. 10a to 10d are graphs illustrating the theoretical response characteristics of the probe shown in FIGS. 9a and 9b.
Figure 10B:
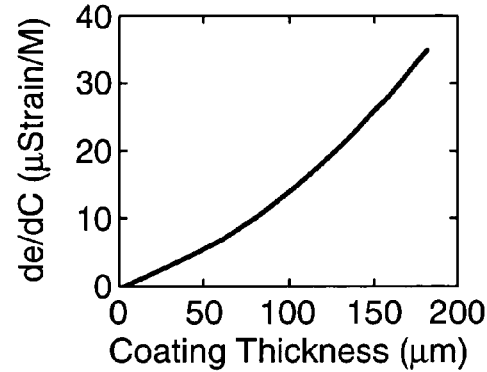
Figure 10C:
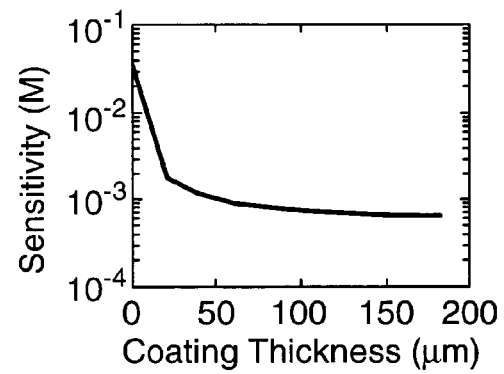
Figure 10D:
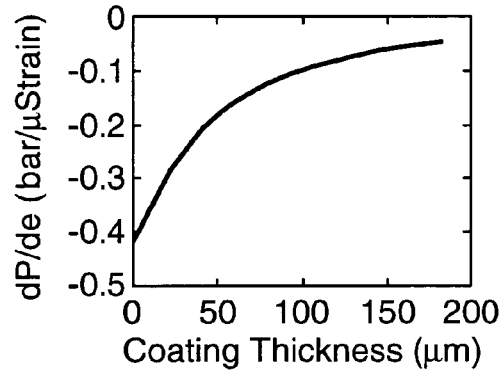

The preferred coating is ionic NIPA polymer gel copolymerised by sodium acrylate (SA), which exhibits significant swelling in an ionic solution. This is a result of an increase in osmotic pressure within the gel due to mobile counter ions and bound cations. FIG. 10a shows the theoretical radial pressure change per Molar change in counter ion concentration as a function of layer thickness, whereas FIG. 10b shows the longitudinal strain change per Molar change in counter ion concentration, again as a function of layer thickness. This is calculated in relation to a fused silica optical fiber with a 125 $\mu$m diameter, for a NIPA-SA gel with a crosslinking density of $10^{19}/cm^3$ and a dry gel volume fraction of 7.5%. The sensitivity to counter ion concentration (FIG. 10c) is determined by the pressure sensitivity of the fiber sensor, here a DFB fiber laser in a side-hole fiber with 1 mbar pressure resolution. For thin coating layers the pressure to strain ratio (FIG. 10d) approaches 420 mbar/$\mu$strain as determined by the elastic properties of the optical fiber. For a fiber without side-holes $P/\varepsilon_z=E/2(1-v)$, where $E=70$ GPa is the Modulus of Elasticity and $v=0.17$ is the Poisson ratio for fused silica. With typical hole sizes of 15 to 30 $\mu$m a side-hole fiber is expected to give a similar ratio. The pressure to strain ration decreases with increasing coating layer thickness, due to increasing longitudinal strain, resulting in saturation in sensitivity.

The sensitivity to counter ionic concentration can be improved significantly by increasing the E-modulus of the polymer gel by increasing the crosslinking density. Increasing the crosslinking density in the NIPA-SA gel by a factor 4 from $10^{19}$ cm$^3$ to $4*10^{19}/cm^3$ increases the E-modulus by a factor of 4 from 96 to 380 kPa and improves the sensitivity by a factor 8.75 from 70 $\mu$M to 8 $\mu$M for a 200 $\mu$m NIPA-SA layer on a 125 $\mu$m diameter optical fiber.

Figure 11:
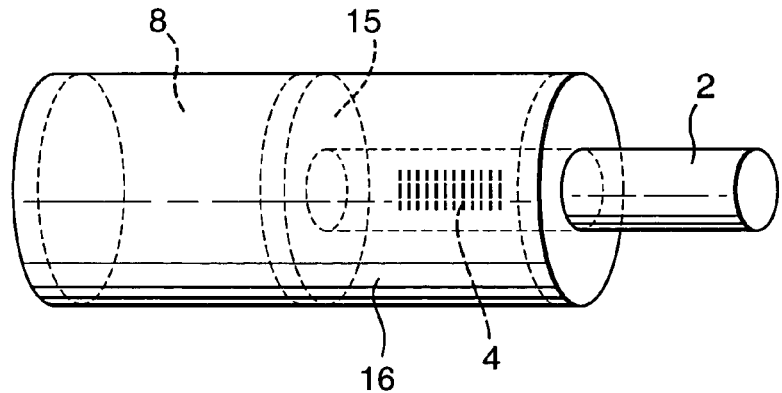
FIG. 11 illustrates, schematically, a further view of the embodiment of the invention shown in FIG. 4.

A further view of the embodiment of the invention shown in FIG. 4 is shown in FIG. 11. This is an arrangement of sensing element 8 in the form of a hydrogel material provided within a cylinder 16, and cooperating with a piston 15 carried by the end of the fiber 2. The sensing material expands or contracts in response to a measurand, which can be a chemical substance diffusing into the cylinder. This establishes longitudinal strain and in turn results in a positive or negative shift in the Bragg wavelength of the FBG 4, which can be an active or passive device. The preferred swelling material for this embodiment is a NIPA-SA gel, with a crosslinking density of $10^{19}/cm^3$ and a dry gel volume fraction of 7.5%. The sensitivity of the probe to mobile counter ion concentration may again be determined theoretically.

Figure 12A:
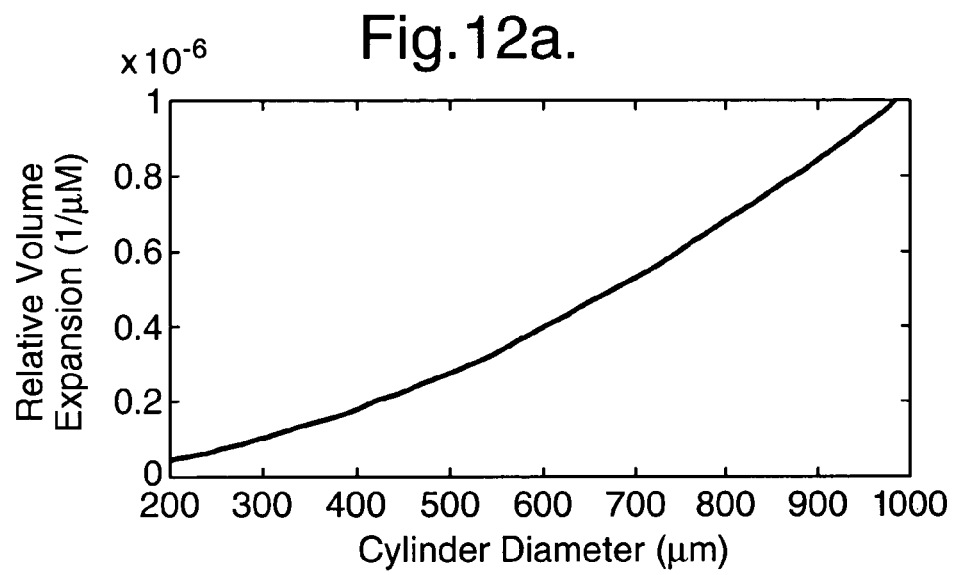
FIGS. 12a and 12b are graphs illustrating the theoretical response characteristics of the probe shown in FIG. 11.

FIG. 12a shows the relative volume expansion per $\mu$ Molar change in counter ion concentration of the cylinder filled with NIPA-SA polymer gel as a function of the diameter of the cylinder. The expansion is working against a 125 $\mu$m diameter fused silica fiber.

Figure 12B:
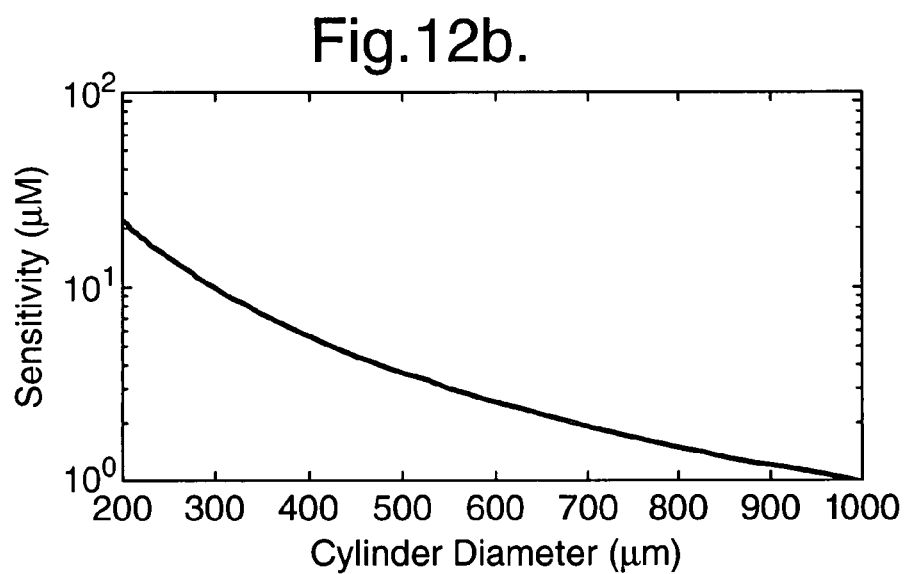

FIG. 12b shows the sensitivity of the optical fiber probe as a function of NIPA-SA cylinder diameter with the FBG interrogation system assumed to have a resolution of 1 microstrain.

FIGS. 13a and 13b show further embodiments of a probe having a side-hole fiber, in which the sensing element 8 is again a hydrogel material coated on the fiber. The embodiment shown in FIG. 13b, like the embodiments described above and shown in FIGS. 8a and 8b, comprises a rigid sleeve 22 which encloses the sensing element 8.

The embodiment of FIG. 13a omits the sleeve. The fiber core 5 may be provided with a passive FBG or a fiber DFB laser, and the sensing element 8 may expand or contract in response to a particular measurand, which can again be a chemical substance diffusing into the layer.

FIG. 14a shows the equivalent pressure at the fiber cladding as a result of relative volume expansion of the coating in the two embodiments. The lower trace shows the pressure without the rigid sleeve, and the upper trace shows the pressure with the rigid sleeve. It will therefore be seen that the rigid sleeve increases the equivalent pressure at the fiber cladding by about a factor of 6 for the same volume expansion of the sensing element layer 8. Hence, the rigid sleeve will improve the sensitivity of the sensor probe.

In FIG. 14a, the E modulus of the coating material is 1 MPa, and the fiber has a 125 $\mu$m diameter. The relative volume expansion of the cladding is then $3*10^{-6}$ of a coating on a fused silica optical fiber. As shown in FIG. 14a, the increase in equivalent pressure resulting from the rigid sleeve is approximately the same for a range of sensing element thicknesses.

FIG. 14b indicates the change in equivalent pressure at the fiber cladding with changes in E-modulus of the sensing element layer 8. In this case, the coating thickness is constant, namely 50 $\mu$m. The relative volume expansion is again $3*10^{-6}$ on a fused silica optical fiber with a 125 $\mu$m diameter. The E-modulus of the coating material is varied from 0.1 MPa to 10 GPa. As is shown in FIG. 14b, the equivalent pressure increases with increasing E-modulus of the coating material.

A still further embodiment is shown in FIG. 15. This arrangement is similar to the embodiment shown in FIG. 5, and includes a piston 15, coupled to the fiber 2, mounted within a cylinder 16.

In this embodiment a sensing element 8 is in the form of a hydrogel material, which is provided with a reactive agent arranged to swell due to reagent-analyte binding. Hence, the sensing element 8 is responsive to a particular chemical or biochemical measurand.

In order to compensate for changes in temperature, a similar gel material 8' is provided in a further section of the cylinder, and acts against the sensing element 8. The gel material 8' is not provided with the reagent. Hence, swelling due to other effects such as temperature and pH will act equally on the piston 15 in opposite directions, and will not affect the sensor's optical response.

In this embodiment, the fiber 2 is provided with an active or passive FBG 4 in the region of the cylinder containing the sensing element gel 8, whereas the region of the fiber 2' contained in the other part of the cylinder is not provided with a sensing region, and acts as a "dummy" fiber having the same mechanical properties as the length of fiber in the other part of the cylinder such that proper compensation is obtained.

A further embodiment is shown in FIG. 16a. In this embodiment, the sensing element 8 (which may be of any of the forms discussed above) is arranged to establish bending strain in the fiber 2. This bending strain induces a change in optical birefringence in the fiber which can be measured by known optical means.

As with the other embodiments, the sensing region of the fiber may be provided with a DFB FBG fiber laser, or a passive PI-phase shifted FBG 4, somewhere between the fixed point and the fiber end. The fixed point can be defined on a rigid support housing, shown schematically as 25. For increased sensitivity, the grating component 4 should be placed close to the fixture point.

The change in difference frequency between the two polarization modes of a DFB FBG laser, or between the two reflection notches of a passive grating, is proportional to one over the square of the radius of curvature of the fiber.

The sensitivity for a side-hole fiber is typically is 60 kHz m². With known instrumentation, there is a resolution of 10 kHz for measurements of difference frequency.

With a design based on a side-hole fiber, where the bending acts on a 10 mm long fiber section, with bending corresponding to 2 mm deflection at the end point, it is possible to resolve a swelling induced deflection of less than 50 nm if the grating/laser component 4 is placed next to the fixture point. Hence, a highly sensitive arrangement can be provided.

FIG. 16b shows a modified embodiment in which, as in the embodiment of FIG. 15, a similar sensing element 8', but omitting a chemically reactive material, acts against the sensing element 8. Hence, the sensor can be configured to be responsive only to a particular biochemical or chemical measurand, with the element 8' compensating for changes in temperature and other parameters other than the substance to which the reactive material 8 is responsive.

FIG. 17 shows a further arrangement of optical fiber, which can be configured to measure bending strain. This fiber includes two cores 5, 5', with a DFB FBG fiber laser or a passive PI-phase shifted FBG in each of the two cores. The bending of this fiber can be measured by measuring the splitting in the resonance in the two cores. The change in difference frequency between the two core modes of the laser, or between the two reflection notches of a passive grating, is proportional to one over the radius of the curvature of the fiber. It can be shown that with this system it may be possible to resolve an induced deflection of less than 50 pm of the end point in a 10 mm long fiber section, with bending corresponding to a 2 mm deflection at the end point with the grating component placed close to the fixed point of the fiber.

What is claimed is:

1. A body compatible fiber optic sensor probe for invasive medical use, the probe including:
    a fiber;
    a sensing location at which the fiber is configured to provide at least one detectable changeable optical property responsive to a strain within the fiber;
    at least one sensing element which undergoes a volumetric change in response to an in body parameter to be sensed;
    wherein the sensing element is coupled to the fiber in such a way that the volumetric change induces the strain within the fiber so as to vary the detectable changeable optical property;
    wherein said fiber has a fiber cladding and comprising at least one sensing location provided with a sensing element in the form of a reactive coating which is disposed directly or indirectly on the fiber cladding, and wherein the coating is configured to create a strain within the fiber responsive to at least one body parameter to be measured, the strain providing a change in at least one detectable optical property of the fiber;
    said probe further comprising a protective membrane arranged over the reactive coating, said membrane allowing measurement of a particular parameter but providing in use a barrier between said coating and a body material, wherein the membrane is arranged to allow selected target molecules to diffuse from the body side through to the coating material forming the sensing element.

2. A probe as claimed in claim 1 wherein the coating is formed from one or more of a plurality of different materials, each material responsive to a selected physical or chemical parameter within the body.

3. A probe as claimed in claim 2 wherein said parameters are selected from the group comprising temperature, pressure, radiation including non-ionizing radiation and ionizing radiation, a particular chemical or biological substance, and chemical or biological, including immunological, interactions.

4. A probe as claimed in claim 1 wherein the reactive coating is formed of a body compatible material such that the coating is able in use directly to contact a biological material within the body.

5. A probe as claimed in claim 1 wherein the fiber has a fiber axis and the reactive coating is provided at a number of different regions spaced along the fiber axis.

6. A probe as claimed in claim 1 wherein the sensing element is arranged to engage a piston carried by or coupled to the fiber.

7. A probe as claimed in claim 6 wherein the piston is arranged within a cylinder and the piston/cylinder arrangement is acted on by first and second sensing elements arranged to apply force to the fiber in opposite directions, the first and second sensing elements each providing a similar response in relation to a first set of parameters, but a different response in relation to a selected measurand.

8. A probe as claimed in claim 1 wherein the sensing element is contained within a cylinder.

9. A probe as claimed in claim 8 wherein the sensing element is a solid or semi-solid material located within the cylinder.

10. A probe as claimed in claim 8 wherein the sensing element is a flowable liquid or gel which expands within the cylinder.

11. A probe as claimed in claim 8 wherein the measurand to be sensed is temperature and the cylinder is formed of a material having a good thermal conductivity.

12. A probe as claimed in claim 8 wherein the probe is a sensor for chemical or biological material, and the cylinder is formed of a material provided with means to enable the molecules of the chemical or biological material to be sensed to permeate through the cylinder walls.

13. A probe as claimed in claim 1, wherein the fiber comprises a pair of pi phase-shifted fiber Bragg gratings.

14. A probe as claimed in claim 1, wherein the probe comprises an active fiber laser including said fiber.

15. A body compatible fiber optic sensor probe for invasive medical use, the probe including:
a fiber;
at least one sensing location at which the fiber is configured to provide at least one detectable changeable optical property responsive to a strain within the fiber;
at least one sensing element which undergoes a volumetric change in response to an in body parameter to be sensed;
wherein the sensing element is coupled to the fiber in such a way that the volumetric change induces the strain within the fiber so as to vary the detectable changeable optical property;
wherein a rigid or semi-rigid housing or a sleeve is provided around the fiber at the sensing location or locations thereof, wherein the sensing element is provided in an annular cavity defined between the housing or sleeve and the fiber; and
wherein the sensing element is a chemical or biochemical sensor, and wherein the sleeve or housing is configured to allow the ingress of a target measurand.

16. A probe as claimed in claim 15 wherein a measurand to be sensed is temperature and the sleeve or housing is formed of a material with good thermal conductivity.

17. A probe as claimed in claim 15 wherein the sensing element applies a sideways force on a sensing region of the fibre to establish a bending strain therein.

18. A probe as claimed in claim 17 comprising first and second sensing elements mounted within the housing, said first sensing element being arranged to urge a free end of the fibre in a first direction and said second sensing element being arranged to urge the free end of the fibre in a second direction, said second direction being opposite to the first direction.

19. A probe as claimed in claim 18 wherein said first sensing element is reactive to a particular chemical or biological substance, and the second sensing element is insensitive to said particular chemical or biological substance but is otherwise of similar construction to the first sensing element.

20. A probe as claimed in claim 15 wherein the fiber comprises one or more side holes at the sensing location.

21. A probe as claimed in claim 20 wherein a further sensing element is provided in said side hole.

22. A probe as claimed in claim 15, wherein the fiber comprises a pair of pi phase-shifted fiber Bragg gratings.

23. A probe as claimed in claim 15, wherein the probe comprises an active fiber laser including said fiber.

24. A body compatible fiber optic sensor probe for invasive medical use, the probe including:
a fiber;
a sensing location at which the fiber is configured to provide at least one detectable changeable optical property responsive to a strain within the fiber;
at least one sensing element which undergoes a volumetric change in response to an in body parameter to be sensed;
wherein the sensing element is coupled to the fiber in such a way that the volumetric change induces the strain within the fiber so as to vary the detectable changeable optical property; and
wherein said sensing element comprises a reactive material immobilized on a solid support medium.

25. A probe as claimed in claim 24 wherein the reactive material is mechanically, electrostatically or chemically immobilized.

26. A probe as claimed in claim 24 wherein the solid support medium is a polymer, copolymer, or a glass.

27. A probe as claimed in claim 24 wherein the support medium is inert to the reaction being analysed.

28. A probe as claimed in claim 24 wherein the support itself acts as a selective element.

29. A probe as claimed in claim 28 wherein the solid support is selective through controlled porosity.

30. A probe as claimed in claim 24, wherein the fiber comprises a pair of pi phase-shifted fiber Bragg gratings.

31. A probe as claimed in claim 24, wherein the probe comprises an active fiber laser including said fiber.

32. A body compatible fiber optic sensor probe for invasive medical use, the probe including:
a fiber;
a sensing location at which the fiber is configured to provide at least one detectable changeable optical property responsive to a strain within the fiber;
at least one sensing element which undergoes a volumetric change in response to an in body parameter to be sensed;
wherein the sensing element is coupled to the fiber in such a way that the volumetric change induces the strain within the fiber so as to vary the detectable changeable optical property; and
wherein the sensing element comprises a reactive material dispersed or immobilized in a fluid or gel, wherein the fluid or gel swells or contracts in response to a target measurand.

33. A probe as claimed in claim 32 wherein the optical fiber has a body compatible surface.

34. A probe as claimed in claim 32 wherein the fiber has a length and wherein the probe is provided with a polymer coating along said length.

35. A probe as claimed in claim 32 wherein the probe is sterilised.

36. A probe as claimed in claim 32 wherein the fiber at the sensing location is provided within a rigid or semi-rigid tubular housing.

37. A probe as claimed in claim 36 wherein the housing is perforate.

38. A probe as claimed in claim 32 wherein the sensing location of the fiber is provided with a removable, retractable protective housing.

39. A probe as claimed in claim 32 wherein the diameter of a fiber core of the fiber probe is between 4 and 15 $\mu$m.

40. A probe as claimed in claim 39 wherein the diameter of the fiber core is 6 to 10 μm.

41. A probe as claimed in claim 40 wherein the fiber core diameter is approximately 8 μm.

42. A probe as claimed in claim 32 wherein the fiber has a cladding of a diameter within the range 80 to 200 μm.

43. A probe as claimed in claim 42 wherein the diameter of the fiber cladding is between 100 to 150 μm.

44. A probe as claimed in claim 43 wherein the fiber cladding diameter is approximately 125 μm.

45. A probe as claimed in claim 32 comprising a protective sleeve or housing enclosing the sensing region of the probe, said protective sleeve or housing having a diameter of the order of 0.2 to 2 mm.

46. A probe as claimed in claim 32 wherein the at least one sensing element comprises a mass of reactive material and wherein the mass of reactive material comprises a coating having a coating thickness of between 10 and 1000 μm.

47. A probe as claimed in claim 32 having an overall fibre optic probe length between 10 and 100 mm.

48. A probe as claimed in claim 32 wherein the probe is formed of a single fiber optic element.

49. A probe as claimed in claim 32 wherein the probe is formed of multiple axially connected fiber optic elements, wherein the length of the probe is between 20 and 150 mm.

50. A probe as claimed in claim 32 which comprises at least one sensing location including an active FBG laser or a passive FBG device providing a birefringent optical output or response dependent upon at least one parameter to be measured.

51. A sterile pack including one or more probes as claimed in claim 32.

52. A method of medical or biological treatment, analysis or diagnosis, comprising exposing one or more probes as described in claim 32 to an in body parameter and measuring the parameter by detecting the changeable optical property of the fiber.

53. A probe as claimed in claim 32, wherein the fiber comprises a pair of pi phase-shifted fiber Bragg gratings.

54. A probe as claimed in claim 32, wherein the probe comprises an active fiber laser including said fiber.

55. A body compatible fiber optic sensor probe for invasive medical use, the probe including:
a fiber;
a sensing location at which the fiber is configured to provide at least one detectable changeable optical property responsive to a strain within the fiber;
at least one sensing element which undergoes a volumetric change in response to an in body parameter to be sensed;
wherein the sensing element is coupled to the fiber in such a way that the volumetric change induces the strain within the fiber so as to vary the detectable changeable optical property;
wherein a separate body compatible membrane is provided covering or enclosing the sensing element.

56. A probe as claimed in claim 53, wherein the fiber comprises a pair of pi phase-shifted fiber Bragg gratings.

57. A probe as claimed in claim 55, wherein the probe comprises an active fiber laser including said fiber.

58. A body compatible fiber optic sensor probe for invasive medical use, the probe including:
a fiber;
a sensing location at which the fiber is configured to provide at least one detectable changeable optical property responsive to a strain within the fiber;
at least one sensing element which undergoes a volumetric change in response to an in body parameter to be sensed;
wherein the sensing element is coupled to the fiber in such a way that the volumetric change induces the strain within the fiber so as to vary the detectable changeable optical property; and
wherein the sensing element comprises micro-spherical balls, provided with additives generating chemical selectivity for a selected group of molecules.

59. A probe as claimed in claim 58, wherein the fiber comprises a pair of pi phase-shifted fiber Bragg gratings.

60. A probe as claimed in claim 58, wherein the probe comprises an active fiber laser including said fiber.

61. A body compatible fiber optic sensor probe for invasive medical use, the probe including:
a fiber;
a sensing location at which the fiber is configured to provide at least one detectable changeable optical property responsive to a strain within the fiber;
at least one sensing element which undergoes a volumetric change in response to an in body parameter to be sensed;
wherein the sensing element is coupled to the fiber in such a way that the volumetric change induces the strain within the fiber so as to vary the detectable changeable optical property; and
wherein the sensing element comprises ionic N-Isopropylacrylamide (NIPA) polymer gel copolymerised by sodium acrylate (SA).

62. A probe as claimed in claim 61, wherein the fiber comprises a pair of pi phase-shifted fiber Bragg gratings.

63. A probe as claimed in claim 61, wherein the probe comprises an active fiber laser including said fiber.

64. A body compatible fiber optic probe for invasive medical use having an optical fiber, the probe configured to provide in at least one sensing location an active fiber laser providing a varying optical output in use dependent upon at least one parameter to be measured within a human or animal body,
wherein said active fiber laser comprises a fiber having a fiber cladding and wherein said sensing location is provided with a sensing element in the form of a reactive coating which is disposed directly or indirectly on the fiber cladding, and wherein the coating is configured to create a strain within the fiber responsive to at least one body parameter to be measured, the strain providing a change in at least one detectable optical property of the fiber;
further comprising a protective membrane arranged over the reactive coating, said membrane allowing measurement of a particular parameter but providing in use a barrier between said coating and a body material
wherein the membrane is arranged to allow selected target molecules to diffuse from the body side through to the coating material forming the sensing element.

65. A probe as claimed in claim 75 wherein the coating is formed from one or more of a plurality of different materials, each material responsive to a selected physical or chemical parameter within the body.

66. A probe as claimed in claim 65 wherein the fiber has a fiber axis and the reactive coating is provided at a number of different regions spaced along the fiber axis.

67. A probe as claimed in claim 64 wherein the optical fiber is birefringent.

68. A probe as claimed in claim 67 wherein the fiber comprises one or more side holes at the sensing location.

69. A probe as claimed in claim 68 wherein a sensing element is provided in said side hole.

70. A probe as claimed in claim 69 wherein the fibre is provided with a membrane at a free end thereof allowing a chemical or biological substance to diffuse through the membrane so as to contact the sensing element material within the side-hole.

71. A probe as claimed in claim 64 wherein a separate body compatible membrane is provided covering or enclosing the sensing location.

72. A probe as claimed in claim 64 wherein a coating of paint or bonding material is provided at the sensing location.

73. A probe as claimed in claim 64 wherein a coating of a porous material is provided at the sensing location.

74. A probe as claimed in claim 64 wherein the sensing location of the fiber is provided with a removable, retractable protective housing.

75. A body compatible fiber optic probe for invasive medical use which is configured to provide in at least one sensing location an active fiber laser providing a varying optical output in use dependent upon at least one parameter to be measured within a human or animal body, said probe further comprising at said sensing location at least one sensing element comprising a mass of reactive material,
wherein said sensing element comprises a reactive material immobilized on a solid support medium, said solid support medium acting as a selective element.

76. A probe as claimed in claim 75 wherein the sensing element creates a radial and/or a longitudinal strain within the fiber in such a way as to change an optical response of the fiber.

77. A probe as claimed in claim 75 wherein the sensing element is coupled to the fiber at two or more axially spaced locations.

78. A probe as claimed in claim 77 wherein the sensing element comprises a cylinder fitted over the optical fiber and secured thereto at axially spaced locations.

79. A probe as claimed in claim 77 wherein the cylinder comprises a first end and a second end and wherein said first end engages a flange extending outwardly from the fiber, and said second end of the cylinder is suitably bonded to the fiber.

80. A probe as claimed in claim 75 wherein the sensing element is arranged to engage a piston carried by or coupled to the fiber.

81. A probe as claimed in claim 75 wherein the sensing element applies a sideways force on a sensing region of the fibre to establish a bending strain therein.

82. A probe as claimed in claim 81 comprising first and second sensing elements mounted within a housing, said first sensing element being arranged to urge a free end of the fibre in a first direction and said second sensing element being arranged to urge the free end of the fibre in a second direction, said second direction being opposite to the first direction.

83. A probe as claimed in claim 82 wherein said first sensing element is reactive to a particular chemical or biological substance, and the second sensing element is less sensitive to said particular chemical or biological substance but is otherwise of similar construction to the first sensing element.

84. A probe as claimed in claim 75 wherein the sensing element comprises a hydrogel.

85. A probe as claimed in claim 75 wherein a coating of paint or bonding material is provided at the sensing location.

86. A probe as claimed in claim 75 wherein a coating of a porous material is provided at the sensing location.

87. A body compatible fiber optic probe for invasive medical use having an optical fiber, the probe configured to provide in at least one sensing location an active fiber laser providing a varying optical output in use dependent upon at least one parameter to be measured within a human or animal body,
wherein a rigid or semi-rigid housing or a sleeve is provided around the fiber at the sensing location thereof, wherein a sensing element is provided in an annular cavity defined between the housing or sleeve and the fiber, and
wherein the sensing element is a chemical or biochemical sensor, and wherein the sleeve or housing is configured to allow the ingress of a target measurand.

88. A probe as claimed in claim 87 wherein a measurand to be sensed is temperature and the sleeve or housing is formed of a material with good thermal conductivity.

89. A body compatible fiber optic probe for invasive medical use which is configured to provide in at least one sensing location an active fiber laser providing a varying optical output in use dependent upon at least one parameter to be measured within a human or animal body, said probe further comprising at said sensing location at least one sensing element comprising a mass of reactive material,
wherein the sensing element comprises a reactive material dispersed or immobilized in a fluid or gel, wherein the fluid or gel swells or contracts in response to a target measurand.

90. A body compatible fiber optic probe for invasive medical use which is configured to provide in at least one sensing location an active fiber laser providing a varying optical output in use dependent upon at least one parameter to be measured within a human or animal body, said probe further comprising at said sensing location at least one sensing element comprising a mass of reactive material,
wherein the sensing element comprises micro-spherical balls, provided with additives generating chemical selectivity for a selected group of molecules.

91. A body compatible fiber optic probe for invasive medical use which comprises an optical fiber, the probe having at least one sensing location including an active FBG laser or a passive FBG device providing a birefringent optical output or response dependent upon at least one parameter to be measured within a human or animal body, said probe further comprising a sensing element at said sensing location, said sensing element comprising a mass of reactive material,
wherein the sensing element comprises a reactive material dispersed or immobilized in a fluid or gel, wherein the fluid or gel swells or contracts in response to a target measurand.

92. A probe as claimed in claim 91 wherein the sensing element creates a radial and/or a longitudinal strain within the fiber in such a way as to change an optical response of the fiber.

93. A probe as claimed in claim 91 wherein the sensing element is coupled to the fiber at two or more axially spaced locations.

94. A probe as claimed in claim 93 wherein the sensing element comprises a cylinder fitted over the optical fiber and secured thereto at axially spaced locations.

95. A probe as claimed in claim 94 wherein the cylinder comprises a first end and a second end and wherein said first end engages a flange extending outwardly from the fiber, and said second end of the cylinder is suitably bonded to the fiber.

96. A probe as claimed in claim 91 wherein the sensing element is arranged to engage a piston carried by or coupled to the fiber.

97. A probe as claimed in claim 91 wherein the sensing element applies a sideways force on a sensing region of the fibre to establish a bending strain therein.

98. A probe as claimed in claim 97 comprising first and second sensing elements mounted within a housing, said first sensing element being arranged to urge a free end of the fibre in a first direction and said second sensing element being arranged to urge the free end of the fibre in a second direction, said second direction being opposite to the first direction.

99. A probe as claimed in claim 98 wherein said first sensing element is reactive to a particular chemical or biological substance, and the second sensing element is less sensitive to said particular chemical or biological substance but is otherwise of similar construction to the first sensing element.

100. A probe as claimed in claim 91 wherein a separate body compatible membrane is provided covering or enclosing the sensing element.

101. A probe as claimed in claim 91 wherein the sensing element comprises a coating of paint or bonding material.

102. A probe as claimed in claim 91 wherein the sensing element comprises a coating of a porous material.

103. A probe as claimed in claim 91 wherein the sensing element comprises a hydrogel.

104. A body compatible fiber optic probe for invasive medical use which comprises an optical fiber, the probe having at least one sensing location including an active FBG laser or a passive FBG device providing a birefringent optical output or response dependent upon at least one parameter to be measured within a human or animal body,
wherein said fiber has a fiber cladding and wherein said sensing location is provided with a sensing element in the form of a reactive coating which is disposed directly or indirectly on the fiber cladding, and wherein the coating is configured to create a strain within the fiber responsive to at least one body parameter to be measured, the strain providing a change in at least one detectable optical property of the fiber;
further comprising a protective membrane arranged over the reactive coating, said membrane allowing measurement of a particular parameter but providing in use a barrier between said coating and a body material, and wherein the membrane is arranged to allow selected target molecules to diffuse from the body side through to the coating material forming the sensing element.

105. A probe as claimed in claim 104 wherein the coating is formed from one or more of a plurality of different materials, each material responsive to a selected physical or chemical parameter within the body.

106. A probe as claimed in claim 105 wherein the reactive coating is formed of a body compatible material such that the coating is able in use directly to contact a biological material within the body.

107. A probe as claimed in claim 104 wherein the fiber has a fiber axis and the reactive coating is provided at a number of different regions spaced along the fiber axis.

108. A probe as claimed in claim 104 wherein said optical fiber comprises at least one side hole.

109. A probe as claimed in claim 108 wherein a further sensing element is provided in said side hole.

110. A probe as claimed in claim 109 wherein the fibre is provided with a membrane at a free end thereof allowing a chemical or biological substance to diffuse through the membrane so as to contact the sensing element material within the side-hole.

111. A probe as claimed in claim 104 wherein the sensing location of the fiber is provided with a removable, retractable protective housing.

112. A body compatible fiber optic probe for invasive medical use which comprises an optical fiber, the probe having at least one sensing location including an active FBG laser or a passive FBG device providing a birefringent optical output or response dependent upon at least one parameter to be measured within a human or animal body,
wherein a rigid or semi-rigid housing or a sleeve is provided around the fiber at the sensing location thereof, wherein a sensing element is provided in an annular cavity defined between the housing or sleeve and the fiber, and
wherein the sensing element is a chemical or biochemical sensor, and wherein the sleeve or housing is configured to allow the ingress of a target measurand.

113. A probe as claimed in claim 112 wherein a measurand to be sensed is temperature and the sleeve or housing is formed of a material with good thermal conductivity.

114. A body compatible fiber optic probe for invasive medical use which comprises an optical fiber, the probe having at least one sensing location including an active FBG laser or a passive FBG device providing a birefringent optical output or response dependent upon at least one parameter to be measured within a human or animal body, said probe further comprising a sensing element at said sensing location, said sensing element comprising a mass of reactive material,
wherein said sensing element comprises a reactive material immobilized on a solid support medium, said solid support medium acting as a selective element.

115. A body compatible fiber optic probe for invasive medical use which comprises an optical fiber, the probe having at least one sensing location including an active FBG laser or a passive FBG device providing a birefringent optical output or response dependent upon at least one parameter to be measured within a human or animal body, said probe further comprising a sensing element at said sensing location, said sensing element comprising a mass of reactive material,
wherein the sensing element comprises micro-spherical balls, provided with additives generating chemical selectivity for a selected group of molecules.

116. A body compatible fiber optic probe for invasive medical use comprising an optical fiber, wherein at least one sensing location of the fiber is provided with a reactive coating configured to create strain within the fiber responsive to at least one body parameter to be measured, such strain providing a change in at least one detectable optical property of the fiber, wherein the reactive coating follows the contour of the fiber, and wherein the reactive coating comprises a reactive material dispersed or immobilized in a fluid or gel, wherein the fluid or gel swells or contracts in response to a target measurand.

117. A probe as claimed in claim 116 wherein said fiber comprises a fiber core having one or more fiber Bragg gratings (FBG's) written in the fiber core.

118. A probe as claimed in claim 116 comprising an active fiber laser including said fiber.

119. A probe as claimed in claim 116 which comprises at least one sensing location including an active FBG laser or a passive FBG device providing a birefringent optical output or response dependent upon at least one parameter to be measured.

120. A probe as claimed in claim 116 wherein the coating is formed from one or more of a plurality of different materials, each material responsive to a selected physical or chemical parameter within the body.

121. A probe as claimed in claim 116 wherein the reactive coating is formed of a body compatible material such that the coating is able in use directly to contact a biological material within the body.

122. A probe as claimed in claim 116 further comprising a protective membrane arranged over the reactive coating, said membrane allowing measurement of a particular parameter but providing in use a barrier between said coating and a body material.

123. A probe as claimed in claim 116 wherein the fiber has a fiber axis and the reactive coating is provided at a number of different regions spaced along the fiber axis.

124. A probe as claimed in claim 116 wherein the optical fiber is birefringent.

125. A probe as claimed in claim 124 wherein the fiber comprises one or more side holes at the sensing location.

126. A probe as claimed in claim 116 wherein a separate body compatible membrane is provided covering or enclosing the reactive coating.

127. A probe as claimed in claim 116 wherein the reactive coating comprises a hydrogel.

128. A probe as claimed in claim 116 wherein the sensing location of the fiber is provided with a removable, retractable protective housing.

129. A probe as claimed in claim 116, wherein the fiber comprises a pair of pi phase-shifted fiber Bragg gratings.

130. A body compatible fiber optic probe for invasive medical use comprising an optical fiber and a protective membrane arranged over the reactive coating, said membrane allowing measurement of a particular parameter but providing in use a barrier between said coating and a body material,
wherein at least one sensing location of the fiber is provided with a reactive coating configured to create strain within the fiber responsive to at least one body parameter to be measured, such strain providing a change in at least one detectable optical property of the fiber, wherein the reactive coating follows the contour of the fiber, and wherein the membrane is arranged to allow selected target molecules to diffuse from the body side through to the coating material forming a sensing element.

131. A body compatible fiber optic probe for invasive medical use comprising an optical fiber, wherein at least one sensing location of the fiber is provided with a reactive coating configured to create strain within the fiber responsive to at least one body parameter to be measured, such strain providing a change in at least one detectable optical property of the fiber, wherein the reactive coating follows the contour of the fiber, and wherein the reactive coating comprises a reactive material immobilized on a solid support medium, said solid support medium acting as a selective element.

132. A body compatible fiber optic probe for invasive medical use comprising an optical fiber, wherein at least one sensing location of the fiber is provided with a reactive coating configured to create strain within the fiber responsive to at least one body parameter to be measured, such strain providing a change in at least one detectable optical property of the fiber, wherein the reactive coating follows the contour of the fiber, and wherein the reactive coating comprises micro-spherical balls, provided with additives generating chemical selectivity for a selected group of molecules.

133. A fiber optic sensor comprising an optical fiber whose optical response changes at one or more measuring locations in response to generally radially applied stress, the fiber being surrounded at such location or locations by a rigid or semi-rigid housing or sleeve, a reactive sensing element being provided between the sleeve and the fiber, the element being arranged to swell in response to a measurand in order to provide strain within the fiber and to change its optical response,
wherein the sensing element comprises a reactive material dispersed or immobilized in a fluid or gel, wherein the fluid or gel swells or contracts in response to a target measurand.

134. A probe as claimed in claim 133 wherein said fiber comprises a fiber core having one or more fiber Bragg gratings (FBG's) written in the fiber core.

135. A probe as claimed in claim 133 comprising an active fiber laser including said fiber.

136. A probe as claimed in claim 133 which comprises at least one sensing location including an active FBG laser or a passive FBG device providing a birefringent optical output or response dependent upon at least one parameter to be measured.

137. A probe as claimed in claim 133 wherein a separate body compatible membrane is provided covering or enclosing the sensing element.

138. A probe as claimed in claim 133 wherein the sensing element comprises a hydrogel.

139. A probe as claimed in claim 133 wherein the housing is perforate.

140. A probe as claimed in claim 133 wherein the sensing location of the fiber is provided with a removable, retractable protective housing.

141. A fiber optic sensor comprising an optical fiber whose optical response changes at one or more measuring locations in response to generally radially applied stress, the fiber being surrounded at such location or locations by a rigid or semi-rigid housing or sleeve, a reactive sensing element being provided between the sleeve and the fiber, the element being arranged to swell in response to a measurand in order to provide strain within the fiber and to change its optical response,
wherein said sensing element comprises a reactive material immobilized on a solid support medium, said solid support medium acting as a selective element.

142. A body compatible fiber optic probe for invasive medical use comprising an optical fiber, the probe comprising a sensor element formed from a polymer gel material whose volume changes in response to at least one body parameter to be measured, such change in volume creating strain within the fiber to change at least one detectable optical property thereof.

143. A probe as claimed in claim 142, wherein the fiber comprises a pair of pi phase-shifted fiber Bragg gratings.

144. A probe as claimed in claim 142, wherein the probe comprises an active fiber laser including said fiber.

* * * * *

UNITED STATES PATENT AND TRADEMARK OFFICE
CERTIFICATE OF CORRECTION

PATENT NO. : 7,003,184 B2  
APPLICATION NO. : 09/950252  
DATED : February 21, 2006  
INVENTOR(S) : Erlend Ronnekleiv et al.

It is certified that error appears in the above-identified patent and that said Letters Patent is hereby corrected as shown below:

Title page,
Item [75], Inventors, "Hjeime" should be -- Hjelme --.

Column 20,
Line 53, add -- , -- after "material".
Line 57, delete "75" and replace with -- 64 --.

Signed and Sealed this

Twentieth Day of June, 2006

JON W. DUDAS
*Director of the United States Patent and Trademark Office*